United States Patent
Thompson et al.

(10) Patent No.: US 6,923,908 B1
(45) Date of Patent: Aug. 2, 2005

(54) FILTER APPARATUS

(75) Inventors: Jonathan Thompson, Center City, MN (US); Yuri Gerner, Mendota Heights, MN (US); Carl W. Sims, St. Paul, MN (US)

(73) Assignee: Systec, LLC, New Brighton, MN (US)

( * ) Notice: Subject to any disclaimer, the term of this patent is extended or adjusted under 35 U.S.C. 154(b) by 59 days.

(21) Appl. No.: 10/688,617

(22) Filed: Oct. 17, 2003

(51) Int. Cl.[7] ............................................. B01D 15/08
(52) U.S. Cl. .................. 210/198.2; 210/188; 210/445; 210/449; 210/451; 210/456
(58) Field of Search .......................... 210/188, 198.2, 210/445, 449, 451, 456

(56) References Cited

U.S. PATENT DOCUMENTS

| | | | | |
|---|---|---|---|---|
| 2,607,954 A | * | 8/1952 | Schneider et al. | 264/169 |
| 2,696,818 A | * | 12/1954 | Van Loghem | 604/252 |
| 2,793,016 A | * | 5/1957 | Aghnides | 239/391 |
| 3,695,450 A | * | 10/1972 | Lieberman | 210/449 |
| 3,722,697 A | * | 3/1973 | Burke et al. | 210/451 |
| 3,815,754 A | * | 6/1974 | Rosenberg | 210/445 |
| 4,157,967 A | * | 6/1979 | Meyst et al. | 210/449 |
| 4,288,325 A | * | 9/1981 | Lieberman | 210/449 |
| 4,496,461 A | * | 1/1985 | Leeke et al. | 210/198.2 |
| 4,798,676 A | * | 1/1989 | Matkovich | 210/767 |
| 4,891,133 A | * | 1/1990 | Colvin, Jr. | 210/198.2 |
| 5,423,982 A | * | 6/1995 | Jungbauer et al. | 210/198.2 |
| 5,494,222 A | * | 2/1996 | Chiu | 239/462 |
| 5,595,653 A | * | 1/1997 | Good et al. | 210/289 |
| 6,224,760 B1 | * | 5/2001 | Davies et al. | 210/198.2 |
| 6,527,951 B1 | * | 3/2003 | Tuvim | 210/198.2 |
| 6,811,688 B1 | * | 11/2004 | Hofmann | 210/198.2 |

* cited by examiner

Primary Examiner—Ernest G. Therkorn
(74) Attorney, Agent, or Firm—Haugen Law Firm PLLP

(57) ABSTRACT

A filter apparatus for use in liquid chromatography systems includes a housing component having an open channel formed therethrough for operably receiving fluid transfer tubing in at least a first end thereof, a relatively thin mesh filter component, and a securement component configured to matingly engage with the housing such that the filter component is operably disposed and secured between the housing and the securement component adjacent to and superimposed over a second open end of the channel. The filter apparatus is thus adapted to operably filter chromatographic fluids being drawn through the channels from the second open end and into the fluid transfer tubing.

11 Claims, 4 Drawing Sheets

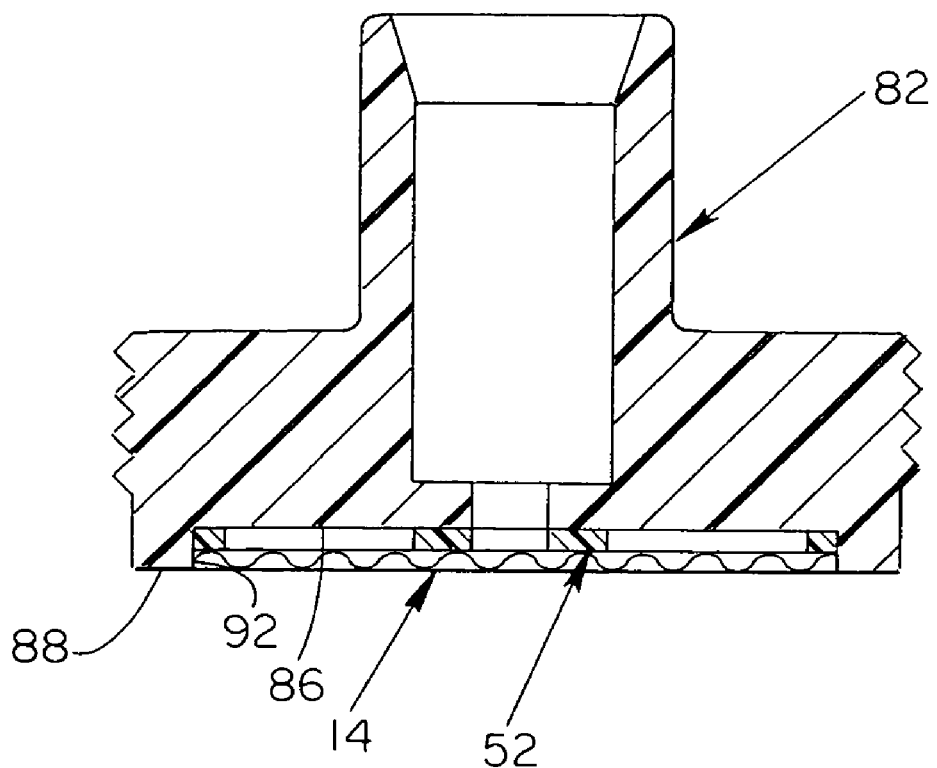

FILTER APPARATUS

FIELD OF THE INVENTION

The present invention relates generally to fluid filters utilized in liquid chromatography systems, and more particularly to a low flow restriction mesh fluid filter that is particularly fabricated to eliminate capillary condensation of gas into the chromatographic fluids being drawn from a fluid reservoir into a liquid chromatography system.

BACKGROUND OF THE INVENTION

Liquid chromatography systems typically draw one or more chromatographic fluids therethrough from corresponding fluid reservoirs. In order to inhibit the infiltration of unwanted debris into the chromatographic system from the respective fluid reservoirs, filter components have been positioned in fluid transfer lines between the fluid reservoirs and the chromatographic system. Such unwanted debris includes, for example, particulate matter that may be harmful to delicate instrumentation incorporated in the respective chromatographic systems. Therefore, an important feature of liquid chromatography systems is the capability to effectively filter unwanted debris from fluid streams entering therein.

A filter component structure commonly utilized in liquid chromatography systems is a sintered porous filter comprising, for example, sintered polytetrafluoroethylene (PTFE), stainless steel, titanium, or glass materials being porously configured so as to provide tortuous paths by which fluid may pass through the filter component. Such sintered filter components are inherently flow restrictive due to the low porosity formed by tortuous fluid paths and long fluid path lengths. These sintered filters have a tendency to increase fluid flow resistance over time as a result of particulate matter being caught up in and blocking respective fluid flow paths. The sintered materials are particularly susceptible to particulate matter retention due to the relatively long and narrow fluid flow paths extending therethrough. Accordingly, particulate matter retention within the sintered filter material blocks subsequent fluid flow through the respective flow paths, therefore resulting in an increased fluid flow resistance through the filter material.

Conventional liquid chromatography systems incorporate proportioning valve units which operably transmit a desired quantity of one or more fluids to the chromatographic column. Pre-pump flow restriction can cause pump and proportioning valve fluid starvation. Typically, such proportioning valve units are calibrated at a predetermined fluid pressure value, such that the accuracy of fluid volume allowed to pass through the valve apparatus depends upon the consistency of fluid pressure immediately upstream from the valve apparatus. As stated above, an issue involving sintered filter materials is the increased flow restriction (back pressure) therethrough as a function of operating time. Correspondingly, fluid pressure between such sintered filter components and valve units decreases over time as the sintered component becomes increasingly blocked due to particulate matter retention therein. It necessarily follows that fluid flow through the valve unit on a predetermined timed basis varies with operational time, thereby having a detrimental effect on fluid volume input accuracy.

An additional issue associated with the use of Teflon fluoropolymers in sintered filter components is the tendency of such components to foster an environment for the formation of gas bubbles that are transferred into the fluid stream flowing therethrough. For example, the capillary structure of a sintered filter component is initially saturated with air within its porous structure. Such air filled capillary inclusions and various surface defects within the sintered structure are nucleation centers for cavitations in the fluid under flow. In sintered filter embodiments of Teflon-type material, the cavity at the nucleation site will tend to grow to a critical level, wherein the viscous drag over the cavity and the equalization of surface energy forces act to release a gas-vapor filled cavity bubble into the continuously flowing fluid stream. Gas bubbles entrained within chromatographic fluids are problematic in that such bubbles lead to inaccurate eluent proportioning, check valve death, measurement drift, and other analytical measurement errors. As such, the minimization and elimination of all sources of gas bubble creation within the chromatographic fluids is highly desired.

It is therefore a principle object of the present invention to provide a fluid filtration component adaptable to liquid chromatography systems, which filter component inhibits the formation of gas bubbles within the fluid stream passing therethrough, and minimizes or eliminates the increased pressure drop over time that is due to particulate matter buildup within fluid paths of the filter component.

It is a yet further object of the present invention to provide a relatively thin screened filter component having a minimal fluid flow restriction therethrough.

It is a still further object of the present invention to provide a mesh filter component for use in liquid chromatography systems, which mesh filter is fabricated from polymeric and metal monofilaments.

It is an additional object of the present invention to provide a filter with a negligible dirt holding capacity.

It is another object of the present invention to provide an apparatus for housing a filter component for use in liquid chromatography systems, wherein the filter housing apparatus incorporates a flow distribution means therein.

It is a further object of the present invention to provide a filter housing apparatus for use in liquid chromatography applications, which filter housing apparatus is readily adaptable to conventional chromatographic fluid transfer lines.

SUMMARY OF THE INVENTION

By means of the present invention, a filter apparatus for use in liquid chromatography systems is specifically configured and fabricated so as to inhibit the formation of gas bubbles in a chromatographic fluid flow stream passing therethrough, as well as to minimize fluid pressure drop therethrough. The filter apparatus of the present invention utilizes a relatively thin screened filter component that is preferably fabricated from a material which more preferentially wets the chromatographic fluid over air compared to fluoropolymers. The so-constructed mesh filter component is preferably operably positioned and secured and sealed in a housing adapted to operably receive chromatographic fluid transfer lines therein.

In a particular embodiment, the filter apparatus of the present invention includes a connection means having an open channel formed therethrough that is configured to operably receive and sealingly engage fluid transfer tubing in at least a first end thereof, and a filtering means comprising a mesh element of between about 0.01 and about 1.0 mm in thickness, and which filtering means has a plurality of apertures disposed therein which are between about 0.2 and about 30 μm in mean diameter. The filter apparatus further includes a securement means configured to matingly engage with the connection means such that the filtering means is operably disposed, secured, and sealed between the connection means and the securement means adjacent to and superimposed over a second open end of the channel, with the filter apparatus being adapted to operably filter chromatographic fluids being drawn through the channel from the second open end and into the fluid transfer tubing.

Preferably, the filtering means is fabricated by weaving PEEK monofilaments together in a reverse Dutch weave configuration. In some embodiments of the present invention, the filter apparatus further includes a flow distributing means disposed between the filtering means and the connection means, and superimposed over the second open end of the channel such that chromatographic fluids being drawn through the filtering means subsequently pass through respective apertures in the flow distributing means, and into the channel.

In another embodiment of the present invention, the filter apparatus includes a housing having an upper end and a lower end, and an open channel extending therebetween, which channel is configured to operably and sealingly receive fluid transfer tubing at least partially therein, said lower end having a recessed portion encompassing a first open end of the open channel corresponding to said lower end of said housing, said recessed portion defining a perimeter protrusion portion extending at least partially therearound and downwardly from said lower end; and a filtering means comprising a mesh element of between about 0.01 and about 1.0 mm in thickness and being formed from a plurality of distinct monofilaments weaved together in a pattern defining a plurality of apertures of between about 0.2 and about 30 $\mu$m in mean diameter, said filtering means having an outer dimension specifically sized so as to be operably press-fit into said recessed portion of said housing with said filtering means being superimposed over said first open end of such channel, said filter apparatus thereby being adapted to operably filter chromatographic fluids being drawn through the channel from said first open end and into the fluid transfer tubing.

BRIEF DESCRIPTION OF THE DRAWINGS

FIG. 8 an isolation view of a component of the filter apparatus of the present invention;

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
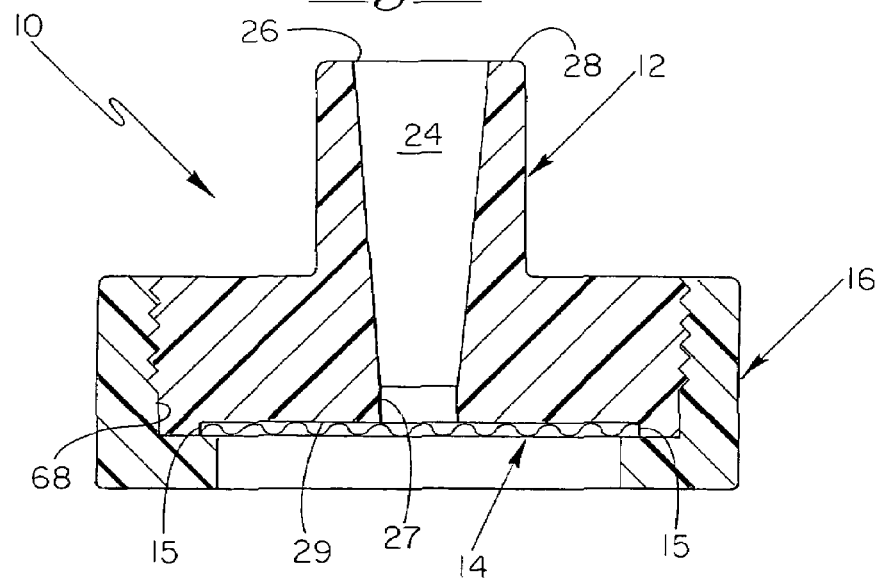
FIG. 1 is a cross-sectional of a filter apparatus of the present invention.

With reference now to the drawing figures, and first to FIG. 1, a filter apparatus 10 of the present invention includes a connection means 12, a filtering means 14, and a securement means 16 that is configured to operably secure and seal filtering means 14 within filter apparatus 10. Connection means 12, filtering means 14, and securement means 16 are preferably individual components that are configured to be selectively engageable with one another, though apparatus 10 may comprise a single component having filtering means 14 integrated therein.

Connection means 12 preferably includes an open channel 24 formed therethrough and extending from an upper end 28 to a lower end 29 thereof. In such a manner, open channel 24 preferably includes a first open end 26 and a second open end 27 corresponding to respective upper and lower ends 28, 29 of connection means 12. A cross-sectional isolation view of connection means 12 is illustrated in FIG. 3.

Figure 3:
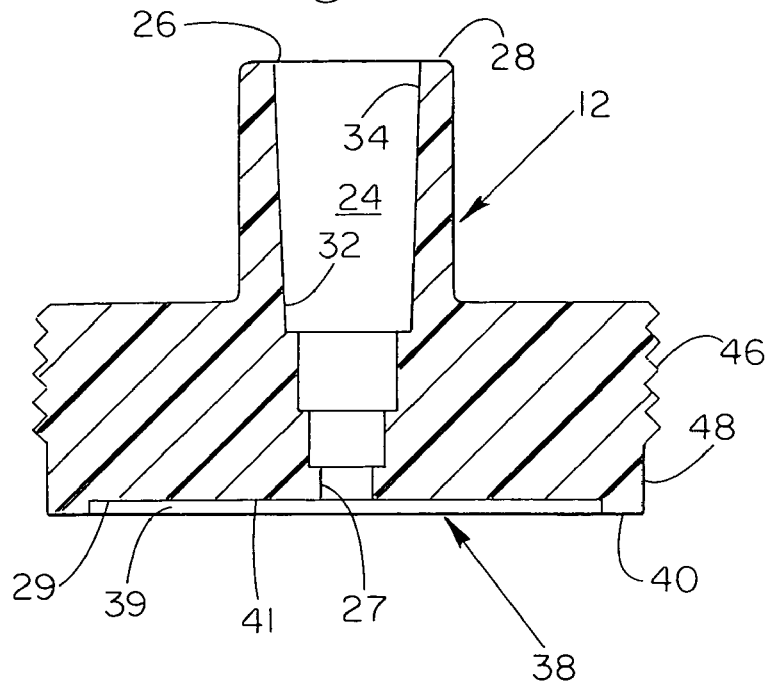
FIG. 3 is an isolation view of a component of the filter apparatus of the present invention.
Figure 4:
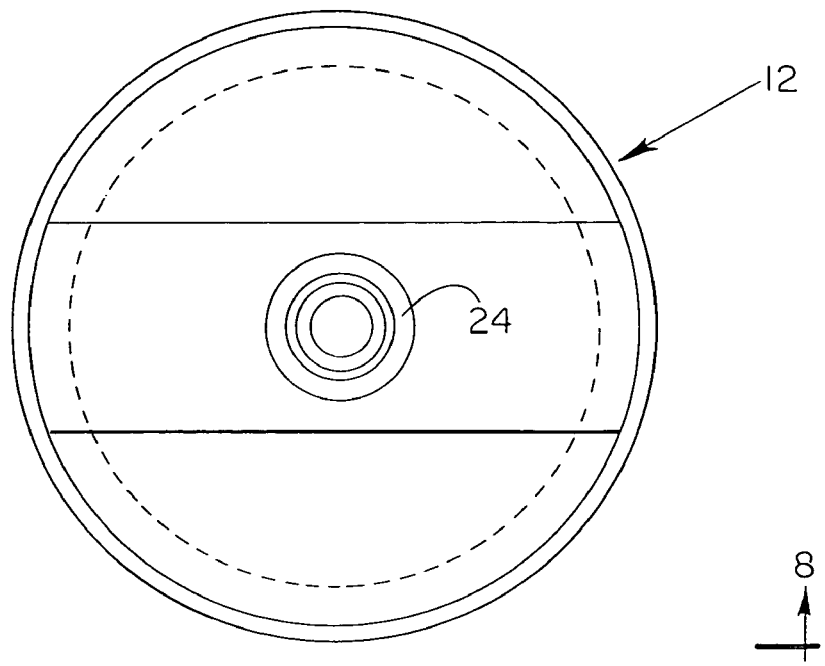
FIG. 4 is a top view of the component illustrated in FIG. 3.

As may be seen more clearly in FIG. 3, first open end 26 of channel 24 is preferably configured so as to operably and sealingly receive fluid transfer tubing therein. In preferred embodiments of the present invention, at least a portion of boundary wall 32 of open channel 24 is threaded so as to threadably receive such fluid transfer tubing in a secure manner. Thus, transfer tubing positioned in channel 24 may be self-threaded by internal threads 34 on wall 32, thereby securely positioning such fluid transfer tubing at least partially within channel 24. Other methods for securely and sealingly positioning the fluid transfer tubing at least partially within channel 24 are contemplated by the present invention, including the utilization of separate securement implements such as ferrules. Second open end 27 of channel 24 is preferably relatively smaller in diameter than first open end 26 of channel 24, such that a controlled fluid flow rate through channel 24 may be maintained.

As is further shown in FIG. 3, lower end 29 of connection means 12 preferably includes a recessed portion 38 disposed within an outer annular ring portion 40. Recessed portion 38 provides a head space within which filtered fluid may be drawn into open channel 24 at second open end 27 thereof. With reference to FIG. 1, filtering means 14 is preferably operably juxtaposed against annular ring portion 40 of connection means 12, such that a gap 39 is formed between recessed portion 38 and filtering means 14 to thereby create the head space so defined. In addition, annular ring portion 40 acts to operably bear a respective peripheral portion 15 of filtering means 14 against securing means 16.

In other embodiments of the present invention, peripheral portion 15 of filtering means 14 may be adhered to annular ring portion 40 via a distinct annular ring that is heat pressed unto peripheral portion 15 of filtering means 14. Such a heat pressed engagement preferably prevents small particles from passing around an outer extent of filtering means 14, in that the seal formed thereby is preferably liquid-tight. Preferably, the separate annular ring is fabricated from a polymeric material such as FEP.

Figure 2:
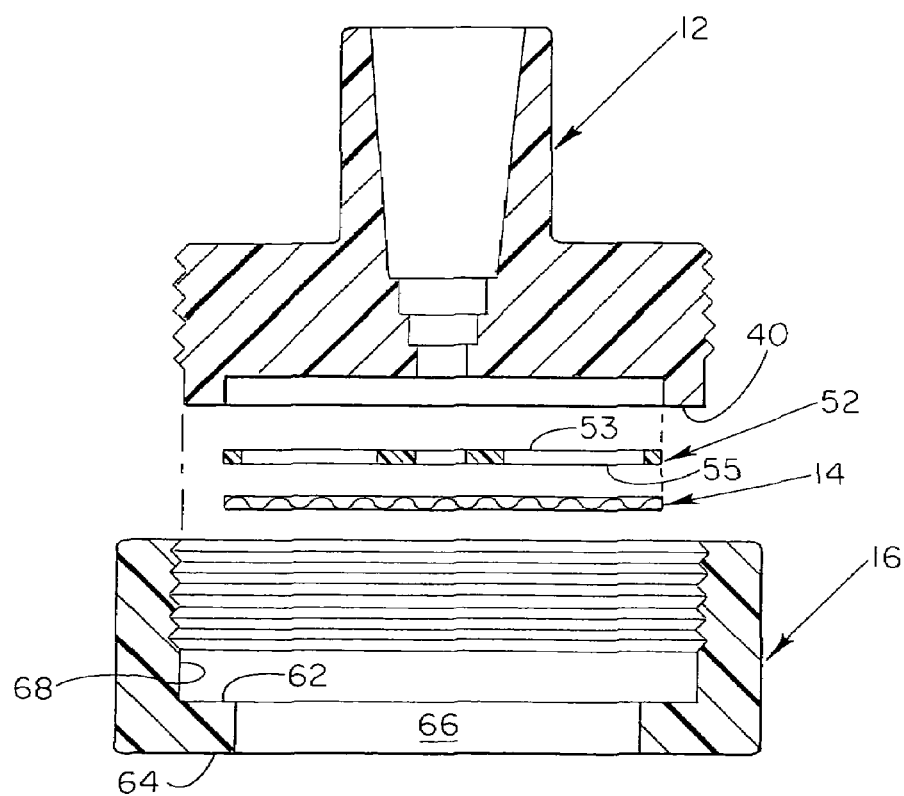
FIG. 2 is a cross-sectional of a filter apparatus of the present invention.
Figure 5:
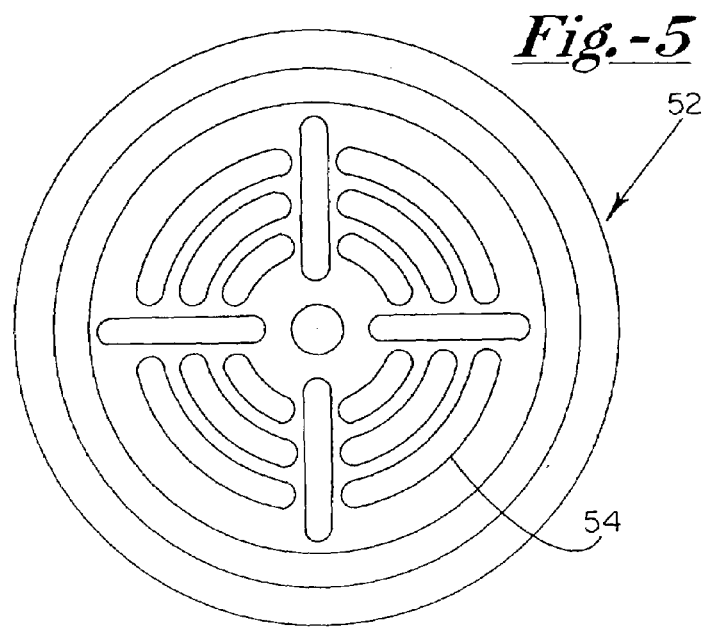
FIG. 5 is an isolation view of a component of the filter apparatus of the present invention.
Figure 6:
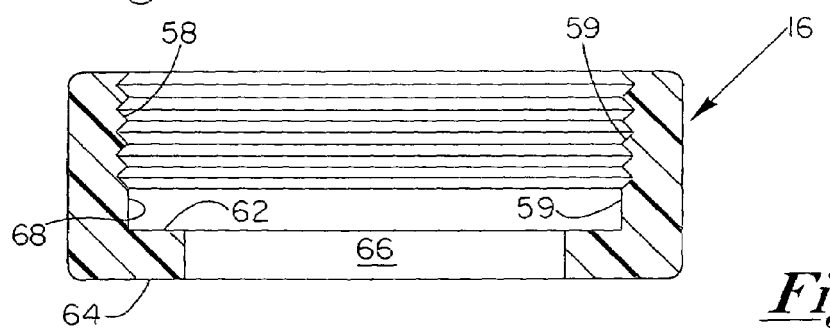
FIG. 6 is a cross-sectional of the filter apparatus of the present invention.

In some embodiments of the present invention, and as illustrated in FIGS. 2, 5, and 6, a flow distribution means 52 may be disposed or integrally formed within the boundary defined by annular ring portion 40 of connection means 12, and adjacent to recessed portion 38 thereof. Flow distributing means 52 is preferably a structure including a plurality of apertures 54 disposed therein. Apertures 54 are preferably configured and positioned in flow distributing means 52 so as to evenly direct and distribute fluid flow therethrough and into second open end 27 of channel 24. In some embodiments of the present invention, flow distributing means 52 is substantially planar, while in other embodiments a portion of flow distributing means 52 may protrude away from, or toward recessed portion 38 of connection means 12 when positioned in gap 39 within the peripheral boundary defined by annular ring portion 40. Preferably, a non-planar flow distributing means 52 extends between about 0.005 inches to about 0.25 inches out from a plane defined by an outer annular portion thereof.

With reference back to FIGS. 1–3, connection means 12 preferably includes threads 46 on a side surface 48 thereof, which threads 46 are configured so as to threadably receive securement means 16 thereon via correspondingly threads 58 on an inner surface 59 of securement means 16. In other embodiments, however, securement means 16 matingly engages with connection means 12 through mating configurations other than corresponding threads. For example, securement means 16 may snappingly engage about outer surface 48 of connection means 12. The friction fit enabled through such mating engagement positively and selectively attaches securement means 16 to connection means 12. Preferably, however, engagement between securement means 16 and connection means 12 is removable, such that a user may selectively engage and disengage securement means 16 to connection means 12. Such removable engagement allows for periodic and desired replacement of filtering means 14 from within filter apparatus 10. Though such replacement is not anticipated by the present invention as being a necessary procedure, such replacement may be performed in order to selectively provide apparatus 10 with a filtering means 14 having particular filtering characteristics.

In the embodiment illustrated in FIG. 2, flow distributing means 52 is preferably disposed adjacent to recessed portion 38 within a boundary defined by annular ring portion 40 of connection means 12, with a first side 53 of filtering means 52 being in facing relationship with lower surface 41 of recessed portion 38, and second side 55 being generally disposed away from surface 41. Filtering means 14 is preferably disposed adjacent to and superimposed over second side 55 of flow distributing means 52, with an outer perimeter portion of filtering means 14 extending beyond an outer periphery of flow distributing means 52. Such an outer periphery portion of filtering means 14 is preferably operably disposed between annular ring portion 40 of connection means 12 and upper surface 62 of annular lip portion 64 of securement means 16. Preferably, filtering means 14 is secured in place between connection means 12 and securement means 16 through a relatively tight engagement therebetween. In the embodiment illustrated in FIG. 2, one or more chromatographic fluids operably flow through opening 66 of securement means 16 as defined between annular lip portion 64 as a result of pressure applied via transfer line tubing operably coupled to connection means 12 at channel 24, and to a fluid pump (not shown). Fluid passing through opening 66 subsequently flows through filtering means 14, wherein particulate matter larger than the apertures defined by filtering means 14 is prevented from passing therethrough, and stays in the bulk fluid contained in the fluid reservoir from which such chromatographic fluid is being drawn. Once through filtering means 14, the fluid is directed through apertures 54 in flow distributing means 52, so as to provide for low flow resistance between filtering means 14 and second open end 27 of open channel 24 in connection means 12. Preferably, therefore, apertures 54 in flow distributing means 52 are spaced from surface 41 of recessed portion 38 so as to maintain an adequate head space between surface 41 and flow distributing means 52 for desired fluid flow therethrough.

Filtering means 14 is preferably a relatively thin mesh configuration providing a plurality of apertures having a mean diameter substantially equivalent to the particulate matter that is desired to be retained in the retentate of the chromatographic fluid reservoir. Preferably, filtering means 14 is between about 0.01 and about 1.0 mm in thickness, and more preferably between about 0.05 and about 0.25 mm in thickness. The present invention, however, contemplates a wide variety of thicknesses for filtering means 14 as desired per application. In a particular embodiment of the present invention, the mesh configuration of filtering means 14 is formed by laying up a plurality of monofilaments into a mesh pattern. The overall thickness for filtering means 14, therefore, directly corresponds to the thickness for the monofilaments used, as well as the type of weave pattern incorporated into the mesh configuration. In certain embodiments of the present invention, filtering means 14 is constructed through a reverse Dutch weave pattern of monofilaments. Other weave patterns, however, such as double weaves and the like may be utilized in forming the mesh pattern of filtering means 14. In some embodiments of the present invention, multiple woven mesh layers are fused together into a multiple-layer construction in order to reduce the effective mean diameter through filtering means 14, as well as to increase the tortuous path through which fluid must flow in order to pass through filtering means 14. Such considerations are employed in applications where a higher degree of filtration is desired.

In preferred embodiments of the present invention, filtering means 14 includes a plurality of apertures defined between respective monofilaments laid up in a mesh pattern. Preferably, such apertures have mean diameters of between about 5 and about 30 $\mu$m, and more preferably between about 10 and about 20 $\mu$m.

Preferably, filtering means 14 is fabricated from a plurality from polymeric and/or metal monofilaments including PEEK, PPS, stainless steel, and titanium. A particularly preferred material for use in such monofilaments is polyether etherketone (PEEK). It has been discovered by the Applicants that monofilaments fabricated from PEEK assist in eliminating the formation of air bubbles in a chromatographic fluid flow environment through the filter apparatus. Specifically, since PEEK materials preferentially wet water over air compared to fluoropolymers, the likelihood of cavity formation in a fluid is substantially diminished. In addition, the thin woven structure of filtering means 14 eliminates the vast majority of capillary sized crevices inherent with sintered materials; thus the bubble nucleation sites are substantially reduced. As a result, the monofilaments of the present invention assist in reducing or eliminating the formation of gas bubbles in the fluid flow stream, and thereby improve overall performance and accuracy of the associated chromatographic system.

In addition to the advantages introduced by the monofilament materials of filtering means 14, the relatively thin mesh configuration thereof inhibits permanent attachment of particulate matter to filtering means 14. In typical chromatographic systems, the fluid pump to which filter apparatus 10 is operably coupled is a positive displacement pump that operates discontinuously in order to inject discrete volumes of fluid into targeted chromatographic components downstream therefrom. Through such a pumping procedure, fluid is only periodically drawn through filter apparatus 10, rather than continuously being drawn therethrough. In such a discontinuous fluid flow regime, particulate matter retained by filtering means 14 is only temporarily held thereagainst during the fluid pump filtration sequence. Thus, when the pump is not actively pumping the respective chromatographic fluid, fluid flow through filter apparatus 10 ceases, thereby allowing retained particulate matter on an upstream side of filtering means 14 to move away from filtering means 14 and into the bulk of the fluid reservoir. Such migration of the particulate matter away from filtering means 14 results in a "self-cleaning" functionality, whereby filtering means 14 is automatically purged of particulate matter retained thereon during an off cycle of the operably coupled pump. Accordingly, fluid flow restriction through filtering means 14 and, correspondingly, fluid pressure drop thereacross, is substantially inhibited through the use of a relatively thin screened filtering means 14, as in the present invention.

By contrast, however, conventional sintered filter materials typically are orders of magnitude thicker than that of filtering means 14 of the present invention. As such, particulate matter retained within conventional sintered filter materials is not able to escape therefrom during the off cycle of the fluid pump. Such an issue is further exasperated due to the highly tortuous path through which particulate matter is filtered from the fluid flowing therethrough, in that such particulate matter is unlikely to be forced backward through a tortuous path without fluid flow pressure thereon. Therefore, without a "backflush" fluid flow on sintered filter materials, no latent force is present to urge the removal of particulate matter from such filters. In the filtering means 14 of the present invention, however, such particulate matter is retained by a single substantially planar layer of mesh material, such that retained particulate matter on an upstream side of filtering means 14 is likely to be removed therefrom through residual currents and other forces within the bulk fluid reservoir in which filter apparatus 10 resides.

Figure 7:
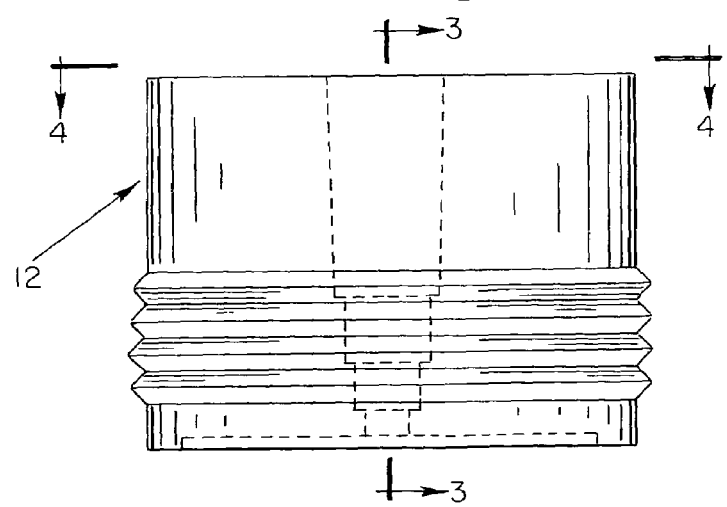
FIG. 7 is an isolation view of a component of the filter apparatus of the present invention.

As illustrated in isolation view in FIG. 7, securement means 16 is specifically configured to matingly engage with connection means 12, in that inner sidewall 59 cooperatively engages with sidewall 48 of connection means 12. Securement means 16 is further provided with annular lip portion 64, which includes an upper surface 62 upon which filtering means 14 finds support in bearing against annular ring portion 40 of connection means 12. Opening 66 is defined within the inner boundary of annular lip portion 64, such that fluid influx through filter apparatus 10 enters through opening 66, and subsequently encounters filtering means 14. As illustrated in FIG. 1, filtering means 14 is preferably sized so as to fit within a boundary defined by inner sidewall 68 of securement means 16.

A side view of connection means 12 of the present invention is illustrated in FIG. 7. An alternative embodiment for the filter apparatus of the present invention is illustrated in FIG. 8, and is designated as 82. Filter apparatus 82 is a unitary component having a recessed portion 86 defining a gap within the inner boundary of annular ring portion 88, with the gap being designated at 92, with gap 92 being specifically configured so as to receive filtering means 14 in a press-fit manner. In some embodiments of the present invention, flow distributing means 52 may be specifically sized so as to be press-fit within gap 92. In such a manner, filter apparatus 82 does not require a distinct securement means as in the embodiment illustrated in FIGS. 1–2.

In preferred embodiments of the present invention, connection means 12 and securement means 16 are fabricated from a relatively durable and inert polymeric material, such as high-density polyethylene and high-density polypropylene. Other materials, however, are contemplated by the present invention as being useful in fabricating the respective components of filter apparatus 10 and filter apparatus 82. Such materials include, for example, metals such as stainless steel, aluminum, and the like, or other inert polymeric materials.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A filter apparatus for use in liquid chromatography systems, said filter apparatus comprising:
   (a) a connection means having an open channel formed therethrough, which channel is configured to operably and sealingly receive fluid transfer tubing in at least a first end thereof;
   (b) a filtering means comprising a mesh element of between about 0.01 and about 1.0 mm in thickness, and having a plurality of apertures disposed therein, such apertures being between about 0.2 and about 30 micrometers in mean diameter; and
   (c) a securement means configured to matingly and sealingly engage with said connection means such that said filtering means is operably disposed and secured between said connection means and said securement means adjacent to and superimposed over a second open end of said channel, said filter apparatus being adapted to operably filter chromatographic fluids being drawn through said channel from said second open end and into the fluid transfer tubing.

2. A filter apparatus as in claim 1 wherein said filtering means is fabricated from PEEK, PPS, or stainless steel.

3. A filter apparatus as in claim 2 wherein said mesh element is formed by weaving PEEK monofilaments together.

4. A filter apparatus as in claim 3 wherein the weave is a reverse Dutch weave configuration.

5. A filter apparatus as in claim 1 wherein said securement means threadably engages with said connection means.

6. A filter apparatus as in claim 1, including a flow distributing means disposed between said filtering means and said connection means, and superimposed over said second open end of said channel, such that chromatographic fluids being drawn through said filtering means subsequently pass through respective apertures in said flow distributing means, and into said channel.

7. A filter apparatus as in claim 6 wherein the apertures in said flow distributing means are spaced thereacross over an area at least as large as the cross-sectional area of said channel at said second open end.

8. A filter apparatus for use in liquid chromatography systems, said filter apparatus comprising:
   a housing having an upper end, a lower end, and an open channel extending therebetween which channel is configured to operably receive fluid transfer tubing at least partially therein, said lower end having a recessed portion encompassing a first open end of the open channel corresponding to said lower end of said housing, said recessed portion defining a perimeter protrusion portion extending at least partially therearound and downwardly from said lower end; and a filtering means comprising a mesh element of between about 0.01 mm and about 1.0 mm in thickness and being formed from a plurality of distinct monofilaments weaved together in a pattern defining a plurality of apertures of between about 5 and about 30 $\mu$m in mean diameter, said filtering means having an outer dimension specifically sized so as to be operably press-fit into said recessed portion of said housing with said filtering means being superimposed over said first open end of such channel, said filter apparatus thereby being adapted to operably filter chromatographic fluids being drawn through the channel from said first open end and into the fluid transfer tubing.

9. A filter apparatus as in claim 8 wherein said filtering means is fabricated from PEEK monofilaments.

10. A filter apparatus as in claim 8, including a flow distributing means disposed between said filtering means and said recessed portion of said housing, and superimposed over said first open end of said channels, such that chromatographic fluids being drawn through said filtering means subsequently pass through respective apertures in said flow distributing means, and into said channel.

11. A filter apparatus as in claim 10 wherein the apertures in said flow distributing means are spaced thereacross over an area at least as large as the cross-sectional area of said channel at said first open end.

* * * * *